(12) United States Patent
Yee et al.

(10) Patent No.: US 10,828,394 B2
(45) Date of Patent: Nov. 10, 2020

(54) ANTI-BACTERIAL ANTI-FUNGAL NANOPILLARED SURFACE

(71) Applicant: The Regents of The University of California, Oakland, CA (US)

(72) Inventors: Albert Yee, Irvine, CA (US); Rachel Rosenzweig, Irvine, CA (US); Mary Nora Dickson, Newport Beach, CA (US); Elena Liang, Irvine, CA (US); Sara Heedy, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 132 days.

(21) Appl. No.: 16/129,411

(22) Filed: Sep. 12, 2018

(65) Prior Publication Data
US 2019/0076573 A1 Mar. 14, 2019

Related U.S. Application Data

(60) Provisional application No. 62/558,131, filed on Sep. 13, 2017.

(51) Int. Cl.
*A61L 27/34* (2006.01)
*A61L 31/10* (2006.01)
(Continued)

(52) U.S. Cl.
CPC .............. *A61L 27/34* (2013.01); *A61L 15/28* (2013.01); *A61L 15/32* (2013.01); *A61L 15/325* (2013.01); *A61L 15/42* (2013.01); *A61L 15/46* (2013.01); *A61L 27/30* (2013.01); *A61L 27/50* (2013.01); *A61L 29/14* (2013.01); *A61L 31/10* (2013.01);
(Continued)

(58) Field of Classification Search
CPC .......... A61L 27/34; A61L 27/30; A61L 31/10; A61L 31/16; A61L 15/28; A61L 15/32; A61L 15/325; A61L 15/42; A61L 15/46; A61L 27/50; A61L 29/14; A61L 31/14;
(Continued)

(56) References Cited

U.S. PATENT DOCUMENTS

| 6,106,552 A | 8/2000 | Lacombe et al. |
| 2003/0175325 A1 | 9/2003 | Chatelier et al. |

(Continued)

FOREIGN PATENT DOCUMENTS

| WO | 2013172794 A1 | 11/2013 |
| WO | 2015055656 A1 | 4/2015 |

(Continued)

OTHER PUBLICATIONS

International Preliminary Report on Patentability for International Application PCT/US2017/021908, Report issued Sep. 11, 2018, dated Sep. 20, 2018, 9 Pgs.

(Continued)

*Primary Examiner* — George J Ulsh
(74) *Attorney, Agent, or Firm* — KPPB LLP

(57) ABSTRACT

The invention relates to surfaces and devices with antibacterial and antifungal properties. In one embodiment, the present invention provides a device comprising a synthetic polymer or biocomposite with antibacterial and antifungal properties, made up of nanopillared and/or micropillared surface structure. In another embodiment, the surface allows flexibility and curvature.

17 Claims, 1 Drawing Sheet

(51) Int. Cl.

| | |
|---|---|
| *A61L 27/30* | (2006.01) |
| *A61L 15/46* | (2006.01) |
| *A61L 31/14* | (2006.01) |
| *A61L 15/28* | (2006.01) |
| *A61L 15/32* | (2006.01) |
| *A61L 27/50* | (2006.01) |
| *A61L 29/14* | (2006.01) |
| *A61L 15/42* | (2006.01) |
| *B82Y 30/00* | (2011.01) |
| *A61F 13/15* | (2006.01) |
| *A61L 31/16* | (2006.01) |

(52) U.S. Cl.
CPC .............. *A61L 31/14* (2013.01); *A61F 13/15* (2013.01); *A61L 31/16* (2013.01); *A61L 2300/406* (2013.01); *A61L 2400/12* (2013.01); *B82Y 30/00* (2013.01)

(58) Field of Classification Search
CPC ........... A61L 2300/406; A61L 2400/12; B82Y 30/00; A61F 13/15
See application file for complete search history.

(56) References Cited

U.S. PATENT DOCUMENTS

| | | |
|---|---|---|
| 2007/0168025 A1 | 7/2007 | Darougar et al. |
| 2007/0227428 A1 | 10/2007 | Brennan et al. |
| 2008/0317982 A1 | 12/2008 | Hecht et al. |
| 2009/0194913 A1 | 8/2009 | Chang et al. |
| 2009/0266418 A1 | 10/2009 | Hu et al. |
| 2010/0036488 A1 | 2/2010 | de Juan, Jr. et al. |
| 2010/0239637 A1 | 9/2010 | Ciolino et al. |
| 2011/0125260 A1 | 5/2011 | Shen |
| 2011/0135814 A1 | 6/2011 | Miyauchi et al. |
| 2011/0160851 A1 | 6/2011 | Mueller-Lierheim |
| 2012/0040461 A1* | 2/2012 | Beachley ............. D01D 5/0076 435/396 |
| 2013/0059113 A1 | 3/2013 | Hatton et al. |
| 2013/0244889 A1 | 9/2013 | Yim et al. |
| 2014/0305904 A1 | 10/2014 | Lan |
| 2015/0104522 A1 | 4/2015 | Xu |
| 2015/0104622 A1 | 4/2015 | Chong et al. |
| 2015/0273755 A1 | 10/2015 | Yee et al. |
| 2019/0075789 A1 | 3/2019 | Yee et al. |
| 2019/0101669 A1 | 4/2019 | Yee et al. |

FOREIGN PATENT DOCUMENTS

| | | |
|---|---|---|
| WO | 2017156460 A1 | 9/2017 |
| WO | 2017160658 A1 | 9/2017 |
| WO | 2017156460 A8 | 5/2018 |

OTHER PUBLICATIONS

International Preliminary Report on Patentability for International Application PCT/US2017/021926, Report issued Sep. 18, 2018, dated Sep. 27, 2018, 7 Pgs.

International Search Report and Written Opinion for International Application No. PCT/US2017/021908, Search completed Jun. 23, 2017, dated Jul. 7, 2017, 12 Pgs.

International Search Report and Written Opinion for International Application No. PCT/US2017/021926, Search completed Apr. 25, 2017, dated Jun. 1, 2017, 8 Pgs.

Banerjee et al., "Antifouling Coatings: Recent Developments in the Design of Surfaces That Prevent Fouling by Proteins, Bacteria, and Marine Organisms.", Advanced Materials, Feb. 11, 2011,vol. 23 Issue 6, pp. 690-718.

Chung et al., "Impact of engineered surface microtopography on biofilm formation of *Staphylococcus aureus*", Biointerphases, Jun. 2007, vol. 2, Issue 2, pp. 89-94.

Hasan et al., "Selective bactericidal activity of nanopatterned superhydrophobic cicada *Psaltoda claripennis* wing surfaces", Appl Microbiol Biotechnol, 2013, vol. 97, pp. 9257-9262.

Ivanova et al., "Natural Bactericidal Surfaces: Mechanical Rupture of Pseudomonas aeruginosa Cells by Cicada Wings", Small, Aug. 20, 2012, vol. 8, Issue16, pp. 2489-2494.

Kirschner et al., "Bio-Inspired Antifouling Strategies, Annual Review of Materials Research", 2012, vol. 42, pp. 211-229.

Kopplmayr et al., "Nanoimprint Lithography on curved surfaces prepared by fused deposition modelling", Surface Topography: Metrology and Properties. Jun. 2015, vol. 3, No. 2, 024003, 12 pgs.

Liu et al., "Bio-Inspired Design of Multiscale Structures for Function Integration, Nano Today", Apr. 2011, vol. 6 issue 2, pp. 155-175.

Pogodin et al., "Biophysical Model of Bacterial Cell Interactions with Nanopatterned Cicada Wing Surfaces", Biophysical Journal vol. 104, Issue 4, 2013 pp. 835-840.

Sun et al., "Wetting properties on nanostructured surfaces of cicada wings", The Journal of Experimental Biology Oct. 1, 2009, vol. 212, Issue 19, pp. 3148-3155.

Yao et al., "Atomic Force Microscopy and Theoretical Considerations of Surface Properties and Turgor Pressures of Bacteria", Colloids and Surfaces B: Biointerfaces 2002, vol. 23, pp. 213-230.

Zhang et al., "Cicada Wings: A Stamp from Nature for Nanoimprint Lithography", Small Dec. 2006, vol. 2 Issue 12, pp. 1440-1443.

Zhang et al., "Surface Modification of Polymethyl Methacrylate Intraocular Lenses by Plasma for Improvement of Antithrombogenicity and Transmittance", Applied Surface Science, vol. 255, pp. 6840-6845, Year (2009).

* cited by examiner

ANTI-BACTERIAL ANTI-FUNGAL NANOPILLARED SURFACE

CROSS-REFERENCE TO RELATED APPLICATIONS

The present application claims the benefit of priority under 35 U.S.C. § 119(e) of provisional application Ser. No. 62/558,131, filed Sep. 13, 2017, the contents of which are hereby incorporated by reference.

FIELD OF THE INVENTION

The present disclosure is in the medical and biomedical field, specifically medical devices.

BACKGROUND OF THE DISCLOSURE

Too often, commonly used medical devices become contaminated by microbes such as bacteria and fungi and pose a threat to human mortality. In 2002, it was estimated that there were approximately 1.7 million hospital associated infections due to medical implant and device contamination. Microbes perilous to human health, such as bacteria and fungi, have evolved to become resistant to antibiotic treatment. Leaders at the 2016 United Nations General Assembly have recently addressed the ongoing battle against antimicrobial resistance as a dominant threat to global health. Microbes such as bacteria and fungi often form detrimental biofilm. Biofilms are complex structures of cellular aggregates that form from microbial cells within an extracellular matrix for survival against the environment, and account for 80% of all infections and contaminated medical implants and devices. In fact, biofilms possess the ability to survive exposure to antibiotic and antifungal treatments as the extracellular matrix reduces diffusion of the drugs into the center of the biofilm masses, reducing exposure of the microbes to drugs. Currently, very few antibacterial and antifungal drugs are even available, and those that exist are often ineffective due to the biofilm. As a result, death rates from such microbial infections are very high and increasing in frequency. Likewise, topical antibiotics lose most of their effectiveness when bacteria are harbored in biofilm matrices. There is an unmet and urgent need for anti-microbial, including both anti-bacterial and anti-fungal, surfaces for commonly contaminated medical implants and devices, such as catheters, contact lenses, and bandages for wounds.

Current solutions for antimicrobial surfaces involve chemical treatment and antibiotic impregnation of medical device surfaces. Limitations to these approaches include diminished chemical potency and the creation of antibiotic resistance. Thus, there is a need in the art for novel and effective antimicrobial and antifungal medical devices, instruments and surfaces.

SUMMARY OF THE INVENTION

Various embodiments include a composite film, comprising a biopolymer blend comprising a nanopillared and/or micropillared surface structure. In another embodiment, the composite film serves as a coating to a medical device. In another embodiment, the composite film is used as part of a catheter. In another embodiment, the composite film is part of a contact lens. In another embodiment, the composite film is the surface of a medical implant. In another embodiment, the biopolymer blend comprises chitin. In another embodiment, the biopolymer blend comprises a blend of chitin, chitosan, gelatin, silk and/or hydrogels. In another embodiment, the biopolymer blend comprises chitin nanofibers embedded in hydrogel matrices of gelatin and chitosan. In another embodiment, the composite film is part of a bandage.

Other embodiments include a method of preventing infection, comprising providing a biopolymer blend comprising a nanopillared and/or micropillared surface structure, and apply the biopolymer blend to a surface as a coating. In another embodiment, the biopolymer blend includes chitin, chitosan, gelatin, or silk, and/or hydrogel. In another embodiment, the surface is a surface to a medical device. In another embodiment, the biopolymer blend has anti-fungal and/or anti-bacterial properties. In another embodiment, the biopolymer blend prevents growth of *Fusarium Oxysporum* and/or *Aspergillus Fumigatus*. In another embodiment, the biopolymer blend prevents growth of *Escherichia coli, Staphylococcus epidermidis*, and/or *Pseudomonas aeruginosa*. In another embodiment, the biopolymer blend comprises chitin nanofibers embedded in hydrogel matrices of gelatin and chitosan. In another embodiment, the biopolymer blend is modified for implementation as a medical implant.

Other embodiments include a antimicrobial composition, comprising biopolymer blend comprising a nanopillared and/or micropillared surface structure. In another embodiment, the biopolymer blend includes chitin, chitosan, gelatin, silk, and/or hydrogel. In another embodiment, the biopolymer blend comprises chitin nanofibers embedded in hydrogel matrices of gelatin and chitosan.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
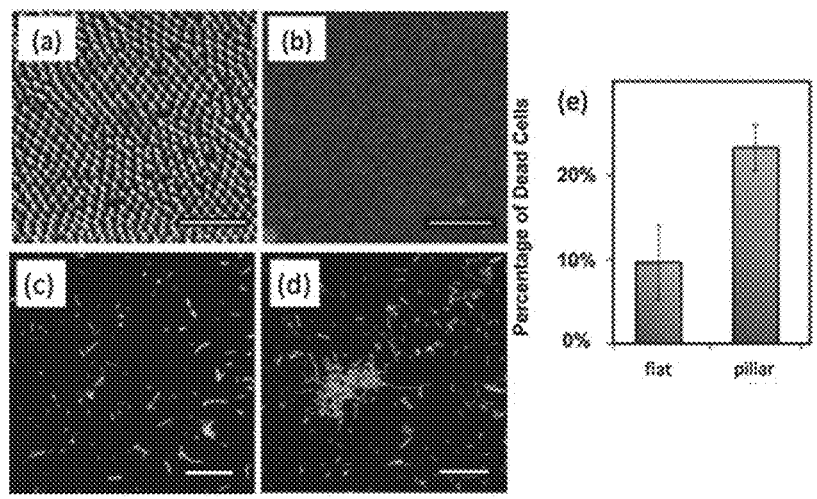
FIG. 1 illustrates, in accordance with embodiments herein, (a) Scanning electron microscopy (SEM) image of uniform PMMA nanopillars with 100 nm diameter (b) SEM image of flat PMMA surface. (c-d) Fluorescence microscopy images of live (green) and dead (red) *Escherichia coli* bacteria on (c) nanopillared and (d) on flat surface. Increased numbers of live bacterial cells observed on flat surfaces. (e) Increase in percentage of dead cells measured on nanopillared surface. Scale bars are 1 µm.
Figure 2:
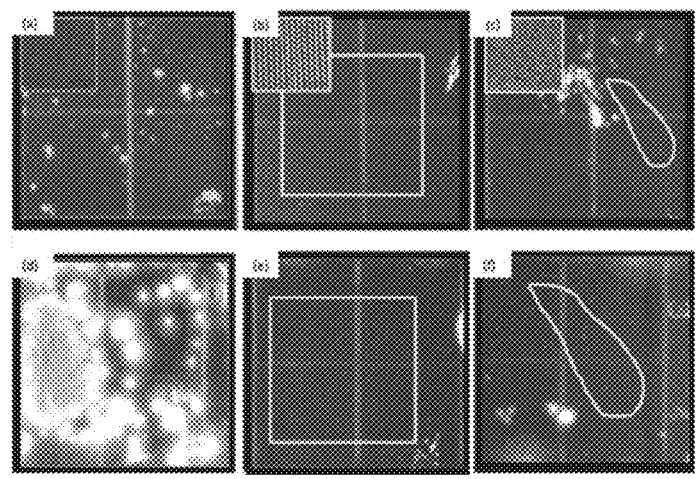
FIG. 2 illustrates, in accordance with embodiments herein, (a) Mold spores (top=*Fusarium oxysporum*; bottom=*Aspergillus fumigatus*) were incubated on PMMA surfaces-(a and d) flat, (b and e) 150 nm diameter pillars and (c and f) 100 nm diameter pillars. Each image area of the surfaces is 25×25 mm. The areas of the surface displaying the nanopillared coating are indicated by light colored outlines. The results show that after incubation, viable mold spores did not survive on the nanopillared surfaces, but survived on the control surface without nanopillars. Insert: SEM images of nanopillars on the test surfaces, scale bars are 1 µm.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "nano" refers to a unit prefix meaning "one billionth", or a factor of $10^{-9}$ or 0.000000001 in the metric system of measurement. For example, as readily apparent to one of skill in the art, the term "nanopillar", refers to pillars that are of a "nano" or very small size. Similarly, the term "micropillar" would refer to pillars that are of a small size, such as a size similar to a factor of $10^{-6}$ (one millionth) in the metric system of measurement.

As used herein, the term "biopolymer blend" also includes biocomposite.

As described herein, in accordance with various embodiments herein, the inventors have developed a novel nanopillared surface that can be applied as a coating on medical implants and devices. In one embodiment, the present invention provides a novel anti-bacterial, anti-fungal nanopillared film that can be formed and applied as a coating onto medical implants and devices. In another embodiment, the present invention provides antibacterial properties of nanopillared surfaces. As described herein, in accordance with another embodiment, generated results on nanopillars imprinted on poly(methyl methacrylate) (PMMA) demonstrate clearly that in areas where there are nanopillars, less *E. coli* adhered and grew on these surfaces over 20 hours. In another embodiment, the present invention provides antifungal properties of nanopillared surfaces. As described herein, in accordance with another embodiment, generated results on nanopillars imprinted on poly(methyl methacrylate) (PMMA) demonstrate clearly that in areas where there are nanopillars, no *Fusarium* or *Aspergillus* fungi adhered and grew on these surfaces over 72 hours.

As further disclosed herein, although PMMA is a suitable material for antimicrobial applications, it is a rigid polymer that does not lend itself easily to applications that require high flexibility, such as coatings typically used on surfaces with small radii of curvature in the mm range, for example, in catheters. In one embodiment, coating is preferably composed from synthetic polymers such as poly(methyl methacrylate), poly(carbonate), poly(ethylene terephthalate), polystyrene, or polyurethane. In another embodiment, the coating is preferably composed from blends of biopolymers such as chitin, chitosan, and hydrogels, such as gelatin or silk. Chitin is known for its biocompatibility, robust mechanical properties, inherent antimicrobial properties, and often used in biomedical applications, such as wound dressing and tissue engineering. Chitin can self-assemble into the matrix of hydrogels such as chitosan, gelatin, or silk as nanofibers to form a flexible yet robust composite film reinforced with the mechanically strong nanofibers. The composite film will have the aforementioned nanopillars for antimicrobial properties, and will possess flexibility and mechanical strength for various medical devices requiring such properties.

In one embodiment, the present invention provides a device, comprising a nanopillared surface structure. In another embodiment, the nanostructured film is a coating to a medical device. In another embodiment, the medical device is a catheter. In another embodiment, the medical device is a contact lens. In another embodiment, the medical device is a medical implant. In another embodiment, the medical device is a bandage.

In another embodiment, the present invention provides a composite film comprising a biopolymer blend comprising a nanopillared and/or micropillared surface structure. In another embodiment, the biopolymer blend includes chitin. In another embodiment, the biopolymer blend comprises chitin nanofibers embedded in hydrogel matrices of gelatin and chitosan.

Other embodiments include a method of preventing infection, comprising providing a biocomposite comprising a nanopillared surface structure, and applying the biocomposite to a surface as a coating. In another embodiment, the surface is a surface to a medical device. In another embodiment, the coating includes synthetic polymers such as poly (methyl methacrylate), poly(carbonate), poly(ethylene terephthalate), polystyrene, polysulfone, polyethersulfone, cyclic olefin copolymer, or polyurethane. In another embodiment, the coating includes blends of biopolymers such as chitin, chitosan, and hydrogels, such as gelatin or silk. In another embodiment, the biocomposite has anti-fungal and/or anti-bacterial properties. In another embodiment, the biocomposite prevents *fusarium* and/or *aspergillus* fungi from proliferation. In another embodiment, the biocomposite prevents *Escherichia coli, Staphylococcus epidermidis*, and *Pseudomonas aeruginosa*.

Embodiments of the present disclosure are further described in the following examples. The examples are merely illustrative and do not in any way limit the scope of the invention as claimed.

EXAMPLES

Example 1

Generally

In one embodiment, the inventors have developed a novel anti-bacterial, anti-fungal surface that can be formed and applied as a coating onto implanted medical devices. Or, for example, bandages. The composite material is preferably composed from blends of chitin, chitosan, and hydrogels, such as gelatin or silk. The novel feature of the composite film is that it incorporates nanopillars to render it antibacterial and anti-fungal. In one embodiment, the present invention is on the antifungal properties of nanopillared surfaces. Results on nanopillars imprinted on poly(methyl methacrylate) (PMMA) demonstrate clearly that in areas where there are nanopillars and/or micropillars, no *Fusarium* or *Aspergillus* fungi adhered and grew on these surfaces over 72 hours. Although PMMA is a suitable material for antimicrobial applications it is a rigid polymer that does not lend itself easily to applications that require high flexibility, such as coatings typically used on surfaces with small radii of curvature in the mm range, for example, in catheters. In one embodiment, the coating includes synthetic polymers such as poly(methyl methacrylate), poly(carbonate), poly(ethylene terephthalate), polystyrene, or polyurethane.

In the present embodiment, the film is preferably composed from blends of biopolymers such as chitin, chitosan, and hydrogels, such as gelatin or silk. Chitin is known for its biocompatibility, robust mechanical properties, inherent antimicrobial properties, and often used in biomedical applications, such as wound dressing and tissue engineering. Chitin can self-assemble into the matrix of hydrogels such as chitosan, gelatin, or silk as nanofibers and/or microfibers to form a flexible yet robust composite film reinforced with the mechanically strong nanofibers and/or microfibers. The composite film will have the aforementioned nanopillars and/or micropillars for antimicrobial properties, and will possess flexibility and mechanical strength for various medical devices requiring such properties. The composite film will have the aforementioned nanopillars and/or micropillars for antimicrobial properties, and will possess flexibility and mechanical strength for various medical devices requiring such properties.

The inventors utilized a composite material comprised of chitin nanofibers embedded in hydrogel matrices of (1) gelatin and (2) chitosan. Chitin, a naturally occurring polysaccharide, is known for its biocompatibility, robust mechanical properties, antifungal properties, and applications in wound healing and drug delivery. Chitosan, a de-acetylated form of chitin, possesses inherent biocompatibility, antimicrobial properties, and ability to store and deliver additional antimicrobial agents. The chitin nanofibers provide mechanical reinforcement to the chitosan or to gelatin without producing turbidity, resulting in optical transparency. The precise mechanical properties are tunable to achieve maximum strength and wearability. Crucially, the material properties could be modified for implementation into different types of medical devices, implants and/or apparatuses.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A composite film characterized by antibacterial and or antifungal properties, comprising:
   a plurality of nanofibers embedded within a hydrogel matrix, and
   at least one surface comprising a plurality of nano- or micropillars, wherein
   the composite film is flexible, yet robust and mechanically strong, and
   at least the surface comprising the plurality of micro- or nanopillars demonstrates antibacterial and or antifungal properties.

2. The composite film of claim 1, wherein the composite film is incorporated as a coating into a medical device such that the medical device displays the plurality of micro- or nanopillars on its surface.

3. The composite film of claim 2, wherein the medical device is a device selected from the group consisting of: a catheter, a contact lens, a medical implant, and a bandage.

4. The composite film of claim 1, wherein the composite film is optically transparent.

5. The composite film of claim 1, wherein the plurality of micro- or nanopillars comprises uniform nanopillars with diameter ranging from 100 to 150 nm.

6. The composite film of claim 1, wherein the plurality of nanofibers and the hydrogel matrix comprise one or a blend of two or more biopolymers selected from the group consisting of: chitin, chitosan, gelatin, silk, another biopolymer fiber material, another biopolymer hydrogel material, and any combination thereof.

7. The composite film of claim 6, wherein the plurality of nanofibers comprises a material selected from the group consisting of: chitin, chitosan, and any combination thereof; and the hydrogel matrix comprises chitosan.

8. The composite film of claim 6, wherein the the plurality of nanofibers comprises chitin; and the hydrogel matrix comprises one or more materials selected from the group consisting of: gelatin, chitosan, silk, and any combination thereof.

9. The composite film of claim 1, wherein the composite film further comprises one or more synthetic polymer materials selected from the group consisting of: poly(methyl methacrylate), poly(carbonate), poly(ethylene terephthalate), polystyrene, polysulfone, polyethersulfone, cyclic olefin copolymer, polyurethane, and another synthetic polymer.

10. A method of preventing a bacterial and or fungal infection proliferation on a surface, comprising:
    providing a substrate of any curvature to be protected against the bacterial and or fungal infection proliferation;
    providing a composite film, comprising:
        a plurality of nanofibers embedded within a hydrogel matrix, and
        at least one surface comprising a plurality of micro- or nanopillars, wherein
    the composite film is flexible, yet robust and mechanically strong; and applying the composite film to the substrate as a coating,
    such that the substrate displays the plurality of micro- or nanopillars on its surface, to obtain a substrate having a nanostructured surface with antibacterial and or antifungal properties.

11. The method of claim 10, wherein the plurality of nanofibers and the hydrogel matrix comprise one or a blend of two or more biopolymers selected from the group consisting of: chitin, chitosan, gelatin, silk, another biopolymer fiber material, another biopolymer hydrogel material, and any combination thereof.

12. The method of claim 10, wherein the substrate comprises a surface of a medical device.

13. The method of claim 10, wherein the plurality of micro- or nanopillars comprises uniform nanopillars with a diameter ranging from 100 to 150 nm.

14. The method of claim 10, wherein the nanostructured surface prevents growth of one or more of the infections selected from the group consisting of: *Fusarium Oxysporum, Aspergillus Fumigatus, Escherichia coli, Staphylococcus epidermidis*, and *Pseudomonas aeruginosa*.

15. The method of claim 10, wherein the composite film is optically transparent.

16. The method of claim 10, wherein the plurality of micro- or nanofibers comprises a material selected from the group consisting of: chitin, chitosan, and any combination thereof; and the hydrogel matrix comprises one or more materials selected from a group consisting of: gelatin, chitosan, silk, another biopolymer hydrogel, and any combination thereof.

17. The method of claim 10, wherein the nanostructured surface with antibacterial and or antifungal properties is incorporated into a medical device selected from the group consisting of: a catheter, a contact lens, a bandage, and a medical implant.

* * * * *

UNITED STATES PATENT AND TRADEMARK OFFICE
CERTIFICATE OF CORRECTION

| | |
|---|---|
| PATENT NO. | : 10,828,394 B2 |
| APPLICATION NO. | : 16/129411 |
| DATED | : November 10, 2020 |
| INVENTOR(S) | : Albert Yee et al. |

It is certified that error appears in the above-identified patent and that said Letters Patent is hereby corrected as shown below:

In the Specification

Column 1, Line 11 The Statement of Federal Funding should read:
STATEMENT OF FEDERALLY SPONSORED RESEARCH
This invention was made with government support under Grant No. W81XWH-17-1-0355 awarded by the U.S. Department of Defense. The government has certain rights in the invention.

Signed and Sealed this
Nineteenth Day of September, 2023

Katherine Kelly Vidal
*Director of the United States Patent and Trademark Office*